United States Patent [19]

Hassler et al.

[11] 4,293,302

[45] Oct. 6, 1981

[54] TOOTH IMPLANTS

[75] Inventors: Craig R. Hassler, Columbus, Ohio; Gary L. Messing, State College, Pa.

[73] Assignee: Scientific Advances, Inc., Columbus, Ohio

[21] Appl. No.: 134,082

[22] Filed: Mar. 26, 1980

[51] Int. Cl.³ ............................................. A61C 7/00
[52] U.S. Cl. ..................................................... 433/173
[58] Field of Search ........................ 433/173, 175, 176

[56]  References Cited

U.S. PATENT DOCUMENTS

| 2,449,522 | 9/1948 | White ................................. | 433/173 |
| 3,589,011 | 6/1971 | Sneer ................................. | 433/174 |
| 3,590,485 | 7/1971 | Chercheve et al. ................ | 433/174 |
| 3,827,145 | 8/1974 | Richards ............................ | 433/175 |
| 3,950,850 | 4/1976 | Driskell et al. . | |
| 4,185,383 | 1/1980 | Helmke .............................. | 433/173 |

FOREIGN PATENT DOCUMENTS 540713  3/1956  Italy .

OTHER PUBLICATIONS

Hassler et al., "Surgical Tooth Implants, Combat and Field", Report No. 5, Contract No. DADA17-6-9-C-9181, Oct. 31, 1974.
Hassler et al., "Surgical Tooth Implants, Combat and Field", Report No. 6, Contract No. DADA17-6-9-C-9181, Oct. 31, 1975.
Hassler et al., "Surgical Tooth Implants, Combat and Field", Report No. 7, Contract No. DADA17-6-9-C-9181, Nov. 30, 1976.
Hassler et al., "Surgical Tooth Implants, Combat and Field", Report No. 8, Contract No. DADA17-6-9-C-9181, Nov. 30, 1977.
Hassler et al., "Surgical Tooth Implants, Combat and Field", Report No. 9, Contract No. DADA17-6-9-C-9181, Dec. 1, 1978.

*Primary Examiner*—Robert Peshock
*Attorney, Agent, or Firm*—Burns, Doane, Swecker & Mathis

[57]  ABSTRACT

An improved dental endosteal implant is disclosed. The implant comprises a base and a core. The base is comprised of a bio-compatible material and has first and second ends and side walls which include serrations having substantially planar surfaces facing in the direction of the second end. The depth of the serrations nearest said second end is greater than the depth of the serrations nearest the first end. The core is configured so as to permit cooperative engagement with at least one prosthetic crown.

32 Claims, 6 Drawing Figures

TOOTH IMPLANTS

The U.S. Government has rights in the present invention pursuant to Contract No. DADA 17-69-C-9181 awarded to Batelle Memorial Institute (Columbus Laboratories) by the U.S. Army Medical Research and Development Command of Ft. Detrick, Md.

BACKGROUND OF THE INVENTION

The present invention relates to dental endosteal implants.

Dental, endosteal implants have been used in recent years which have been rigidly affixed by bone ingrowth with the aid of serrated or porous portions in the body of the implant. Such implants are described in several publications including Hassler et al, "Surgical Tooth Implants, Combat and Field", Reports No. 7 and 8, Contract No. DADA17-69-C-9181 (November, 1976 and December 1977), Hassler et al, "Ceramic Tooth Implants in Baboons", *Journal Dent. Res.*, 56A, A117 (1977), and Hassler et al, "Ceramic Tooth Implants in Baboons", *Trans. Soc. of Biomaterials*, 2, 114 (1978). In addition, U.S. Pat. No. 3,950,850 (issued to Driskell et al on Apr. 20, 1976) discloses dental implants which are suitable for surgical implantation and which include serrated portions in the body thereof.

While the implants described in the Driskell et al patent and the Hassler et al publications (all of which are specifically incorporated herein by reference) have been successfully used in a clinical environment, the use of implants has presented certain problems which prevent conventional dental implants from achieving universal acceptance. For example, failures of the implants have sometimes occurred during the period after implantation when the surrounding bone has grown sufficiently to provide proper support for the implant. Specifically, in those implants which employ a serrated portion to provide support as a result of bone ingrowth, the cross-sectional dimension of certain portions of the implant body is lessened due to the serrations, thus correspondingly reducing the ability of the implant body to withstand transverse loads of large magnitude which are placed upon it. Thus, the implanted bodies are susceptible to fracturing in the area of the bone line along those portions of the implant having the least cross-sectional dimension.

The lessened cross-sectional dimension of certain portions of the implant due to the presence of the serrations can also present other problems. It is difficult to provide serrated dental implant bodies which do not exhibit a certain minimum cross-sectional dimension since the strength of the implant body and its resistance to fracturing would be decreased. Accordingly, it has not been feasible to provide serrated dental implant bodies which are small enough to be implanted into a bone structure which would not normally accommodate an implant of conventional dimension.

In addition, the bone surrounding the implant body frequently atrophies near the upper portion of the implant body (i.e., near the aveolar crest), thus causing a "cratering" effect. The upper portion of the implant body is thus not sufficiently supported by the bone subsequent to implantation and any movement of the upper portion due to a transverse load placed thereon may cause the lower implanted portion to fracture as a result of a "levering" effect.

OBJECTS AND SUMMARY OF THE INVENTION

It is therefore an object of the present invention to provide a dental implant which is more resistant to fracturing subsequent to implantation.

It is also an object of the present invention to provide a dental implant which prevents excessive bone resorption subsequent to implantation.

It is still further an object of the present invention to provide a dental implant which may be smaller in dimension than conventional implants.

It is yet another object of the present invention to obviate the problems of the prior art discussed above.

In one aspect of the present invention there is provided a dental, prosthetic, endosteal implant comprising:
 a base comprised of a bio-compatible material, said base having first and second ends and side walls which include serrations having substantially planar surfaces facing in the direction of said second end, the depth of the serrations nearest said second end being greater than the depth of the serrations nearest said first end, said first end being the outermost end upon implantation and said second end being the implanted end; and
 a core extending from the first end of said base and configured to permit cooperative engagement with at least one prosthetic crown.

In another aspect of the invention there is provided a dental, prosthetic, endosteal implant comprising:
 a base comprised of a bio-compatible material, said base having first and second ends and side walls which include serrations having substantially planar surfaces facing in the direction of said second end, said first end being the outermost end upon implantation and said second end being the implanted end,
 the improvement wherein the depth of the serrations nearest said second end is greater than the depth of the serrations nearest said first end such that the surface area of said planar surfaces is greater nearest said second end than nearest said first end. In still another aspect of the present invention there is provided a prosthetic, endosteal implant comprising:
 a base comprised of a bio-compatible material, said base having first and second ends and side walls which include serrations having substantially planar surfaces facing in the direction of said second end, the depth of the serrations which, upon implantation, are adjacent to the alveolar crest being less than the depth of the serrations in the remaining portion of the base.

DETAILED DESCRIPTION OF THE INVENTION

Figure 1:
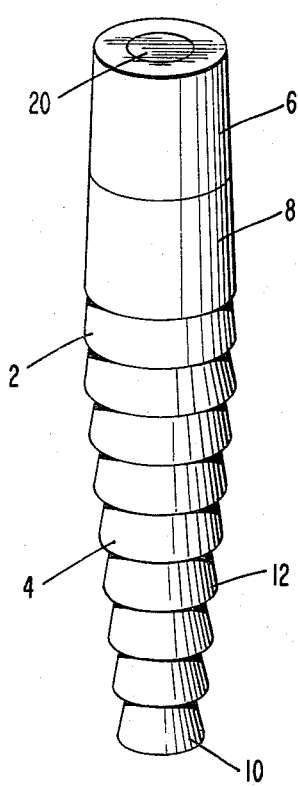
FIG. 1 is a view in perspective of one embodiment of the dental implant body of the present invention.

The dental implant of the present invention will be described with reference to FIGS. 1, 2, 3, 4 and 5.

The implant body 2 includes both a base 4 and a core 6. The base serves as the root for the implant. A prosthetic crown (not shown) is attached to the core upon implantation.

The base 4 includes a first end 8 and a second end 10 axially spaced along the longitudinal axis of the base and serrated side walls 12. The serrations extend along the length of the base and have substantially planar surfaces 14 facing in the direction of the second end 10 and substantially perpendicular to the longitudinal axis of the base. The planar surfaces alternate with oblique surfaces 16 which are disposed at an angle to the longitudinal axis of the implant body.

Figure 2:
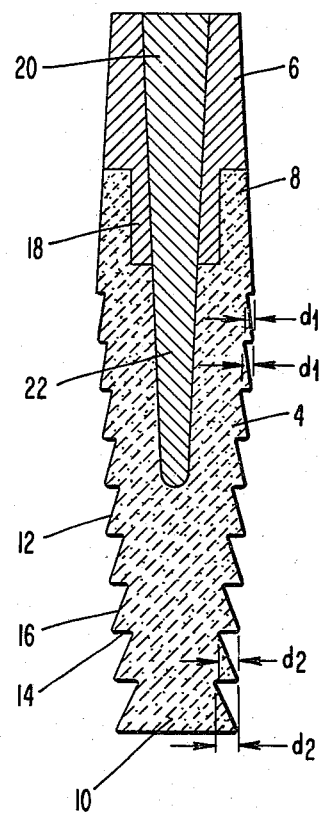
FIG. 2 is a cross-sectional view of the implant body depicted in FIG. 1.
Figure 3:
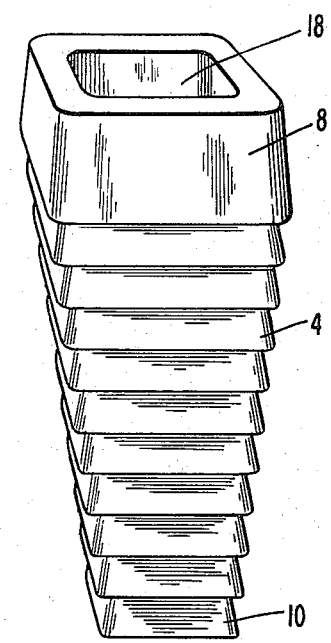
FIG. 3 is a view in perspective of another embodiment of the implant body of the present invention.
Figure 4:
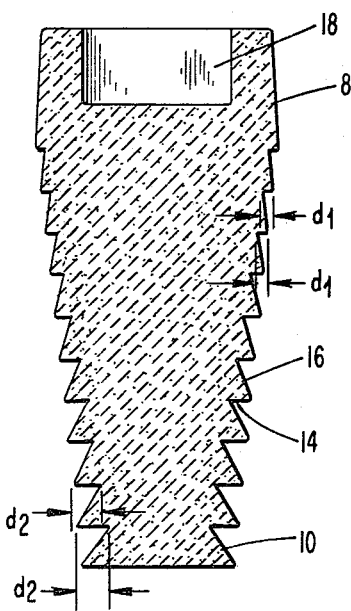
FIG. 4 is a cross-sectional view of the implant body depicted in FIG. 3.

In accordance with the present invention and as illustrated in the Figures, the depth of the serrations (as defined by the length or lateral extent of the respective planar portions) in the side walls 12 is greater nearest the second end 10 than near the first end 8. The depth of each of the serrations may increase in the direction of the second end 10 such that the rate of increase of the depth of the serrations is substantially constant from the first end 8 toward the second end 10 as depicted in FIGS. 1 and 2. In the alternative, the increase in depth may be more gradual as depicted in FIGS. 3 and 4 (e.g., the depth of a group of serrations may be relatively constant while differing from the depth of an adjacent group of serrations).

The change in depth of the serrations in absolute terms from the first end 8 toward the second end 10 is not critical and need only be sufficient to achieve the objects of the present invention (i.e., to provide desired stress concentrations and increased strength). That is, the depth $d_2$ of the serrations nearer to the second end 10 (i.e., the implanted end) must be sufficiently great to provide stability for the implant after the bone has grown sufficiently to encompass and interlock with the serrated portion of the base. In addition, the planar surfaces 14 of these serrations must be provided with sufficient surface area (both individually and as a whole) to dissipate the intended occlusal load which is placed upon the implant in a direction normal to the planar surfaces (and accordingly transferred to the supporting bone) during use.

Figure 6:
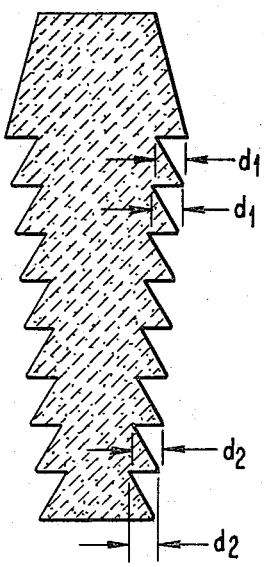
FIG. 6 is a cross-sectional view of a prior art implant body.

The depth $d_1$ of the serrations nearer the first end 8 should be, however, significantly less than the depth of the serrations nearer the second end 10 of the implant body. Preferably, the depth of the serrations nearest the second end is at least about 50 percent greater than the depth of the serrations nearest the first end. Most preferably, the depth of the serrations nearest the second end is at least about 100 percent greater than the depth of the serrations nearest the first end. Such a configuration contrasts with the configuration of the prior art implant body depicted in FIG. 6 wherein the depths $d_1$ and $d_2$ are intended to be substantially equal.

The lessened serration depth nearer the first end (i.e., in those serrations in the area of the alveolar crest upon implantation of the body) provides a lessened surface area for the planar surfaces of those serrations in comparison to the serrations nearest the second end. The lessened serration depth concomitantly provides a greater minimal cross-sectional dimension for the implant body in that portion, thus strengthening that portion of the implant body and increasing its resistance to fracturing when subjected to high loads in a direction transverse to the longitudinal axis of the implant.

As an additional advantage, it is believed that the lessening of the serration depth near the first end aids in the prevention of "cratering" along the bone line. That is, since the occlusal loads which are placed upon the implant body are transmitted to the surrounding bone through the planar portion 14 over a surface area which is less than that normally employed in implant bodies, the stress to which the surrounding bone is subjected is increased in comparison to such prior art implant bodies. Accordingly, since bone normally responds to applied stress by increasing in strength to counteract the stress, it is believed that the bone in the area of the first end will respond to the high stress concentrations in the area of the planar portions by becoming stronger. The surrounding bone should thus not be as likely to atrophy and "cratering" should not occur to the extent observed when conventional implants are employed.

The dissipation of the occlusal load may be controlled by varying the surface area of the planar surfaces such that the stress which is placed upon the supporting bone (expressed as load per unit area) is not so excessive as to initiate stress-induced inhibition of bone remodeling (i.e., avoiding bone resorption) nor so low as to produce bone loss (i.e., such that the bone will not atrophy).

Research has been conducted concerning the optimization of stress as it relates to bone formation and one skilled in the art can therefore determine the magnitude of the planar surface area (and consequently the depth of the serrations) required to optimize the stress on the supporting bone. See, for example, Hassler et al, "Quantitation of Compressive Stress and its Effects Upon Bone Remodeling", *Bulletin of the Hospital for Joint Diseases,* Vol. 38, No. 2, October 1977, pg. 90–93, herein incorporated by reference.

The serrations which begin in the first end will preferably be of a minimal depth so as to provide the lessened surface area. That is, the depth will normally be for purposes of the present invention much less that 1 and preferably 0.5 millimeter or less for an implant body of 4 to 6 millimeters in maximum cross-sectional dimension. A depth of about 0.2 to 0.3 millimeter has been found to be especially suitable. The serrations will generally increase in depth along the longitudinal axis of the implant body toward the second end, with the depth of the serrations nearest the second end being of the greatest depth (e.g., a depth of about 0.75 to 1.0 millimeter or greater depending upon the cross-sectional dimension of the implant body at that point).

Figure 5:
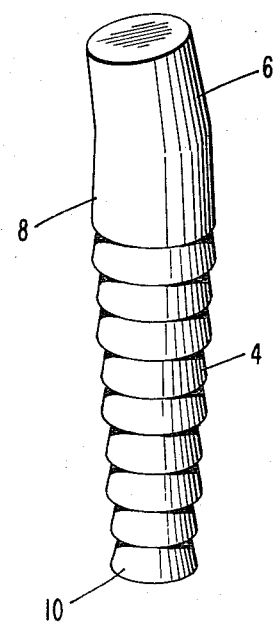
FIG. 5 is a view in perspective of yet another embodiment of the implant body of the present invention.

It is also possible for a number of the serrations nearest to the second end to have substantially identical depths $d_2$ in order to sufficiently dissipate the occlusal load and enable the bone to provide maximum support by interlocking extensively with the base. The serration depth may thus be substantially identical over a significant portion of the length of the base (e.g., fifty percent or so of the length of the base measuring from the second end toward the first end) as depicted in FIG. 5.

Preferably, however, the depth of the serrations in the half of the base nearest the first end will be significantly less then the depth of the serrations in the half of the base nearest the second end. Such a configuration will provide the desired increased structural strength (by increasing the minimum cross-sectional dimension of that portion of the base) as well as the desired reduced surface area in the planar portions in the area adjacent to the alveolar crest upon implantation.

In order to ensure that the structural strength is increased to the necessary extent, the minimum cross-sectional dimension of the portion of the base adjacent to the alveolar crest upon implantation will generally exceed the minimum cross-sectional dimension of the remaining portion of the base. That is, it is possible that the maximum cross-sectional dimension of the base may be substantially the same along its longitudinal axis. However, the minimum cross-sectional dimension may vary due to the varying depth of the serrations, with the minimum cross-sectional dimension nearest the first end being greater than the minimum cross-sectional dimension nearest the second end due to the difference in depth of the serrations nearest the first and second ends.

The degree of taper of the oblique surfaces 16 of the serrations relative to the longitudinal axis of the implant body will similarly increase in proportion to the increase in serration depth. For example, the degree of taper will generally be about 5° or less nearest the first end depending upon the serration depth. However, the degree of taper will correspondingly increase along the longitudinal axis of the implant body to ultimately range between about 20° and 45° nearest the second end.

The base may be comprised of any suitable bio-compatible material. A preferred bio-compatible material for use in the present invention is high density, low porosity alumina. Preferably, the density exceeds about 93 percent of the theoretical with the purity of the alumina being greater than about 98 percent. Suitable high density, high purity alumina is commercially available and includes alumina designated as Alcoa A-16SG and Reynolds RC-HP-DBM.

It is further preferred that the alumina which is used in the formation of the implant body not be susceptible to excessive grain growth which would disadvantageously reduce the density and strength of the implant body. Small amounts of grain growth inhibiters (e.g., magnesia) and other densification agents may advantageously be added to the alumina during formation of the implant body to ensure that the desired high density is achieved. Methods of preparation of such high density, low porosity alumina are well known in the art and will not be discussed further in any greater detail.

The serrations are depicted in the Figures as extending around the entire circumference of the base of the implant body. While such is the preferred practice and is believed to provide the best results, it is possible for only a portion of the side walls of the base of the implant body to include serrations. Even in such an occurrence, however, the serrations would still be configured in accordance with the present invention (i.e., the serration depth would increase from the first end toward the second end).

The base 4 of the implant may be of any suitable shape or configuration. For example, it has been conventional for the base of dental implants to be tapered as shown in the Figures. Such implants are also generally substantially cylindrical and circular or elliptical in cross-section as shown in FIG. 1. It is preferable, however, for the base of the implant to conform to the general configuration of the root of the tooth to be replaced. As such, if only a single tooth is to be substituted for, the cross-section of the base of the implant is preferably substantially rectangular as shown in FIG. 3. If several adjacent teeth are to be replaced by the implant, the base can also be substantially rectangular, although more elongated in cross-section. The configuration of each implant body may be varied to closely conform to the cavity into which the base is to be implanted.

The implant body may be produced in such a manner (e.g., by suitable molding techniques) that an integral base and core is provided (i.e., a single piece implant body having both core and base portions). In the altenative, the base may be adapted to permit attachment of a core thereto. Suitable means of attachment include seating and cementing a portion of the core in a cavity 18 in the base. Typically, the core will include both a bio-compatible portion 6 and a metal post 20. A composite post and core may also be provided which is the functional equivalent of 6 and 20 and is comprised of a suitable material (e.g., a metal). The post is seated in a cavity 22 in the base and provides structural support for both the base and the core supported thereby. The method of preparation of such implant bodies is known in the art and will not be discussed in further detail herein.

It should be noted that when a post and core configuration is employed in the implant, the depth of the serrations disposed laterally from the cavity 22 will preferably be reduced to provide added structural strength since the volume of bio-compatible material in that portion has been reduced by the presence of the cavity. Normally, however, the cavity 22 will not extend beyond the half of the base nearest to the first end 8.

It has been found to be preferable for the implant body to consist of a base and a core which is attached thereto sometime subsequent to implantation of the base. Such delayed attachment of the core to the base minimizes the loads which are placed upon the implanted base prior to the time when the surrounding bone has grown sufficiently to provide the necessary structural support for the base. When the required bone growth has occurred, the core can be attached to the base. When it consists of a separate body, the core can be comprised of any suitable type of material such as metals or bio-compatible materials such as alumina. A prosthetic crown can then be seated on the core and cemented thereto.

The implant body may be configured such that the longitudinal axes of the core and base members substantially coincide. However, it may also be advantageous, depending upon considerations such as the placement of the implant body in the mouth, to configure the core and base such that their longitudinal axes do not coincide but intersect as depicted in FIG. 5. The determination of what configuration is appropriate for a specific circumstance may readily be made by one of ordinary skill in the art.

The implant body may be employed as follows. A tooth socket (e.g., a mandibular or maxillary socket) is enlarged and deepened using a tapered bone burr. A base comprised of high density, high purity alumina, which is of a suitable size and configuration (i.e., substantially rectangular in cross-section) having cross-sectional dimensions of 7×6 mm nearest the first end to provide a suitable fit, is gently tapped into place in the socket. The base is tapped into the socket until the first serration nearest to the first (or outermost) end of the base contacts the aveolar bone. The depth of the serrations nearest to the outermost end of the implant is about 0.3 millimeter, and the depth of the serrations nearest to the implanted end is about 0.75 millimeter. The patient is thereafter given no further attention with the exception of normal post-surgical procedures (e.g., administration of antibiotics, etc.).

After a period of about three to six months, the bone has surrounded and interlocked with the implanted base sufficiently to permit attachment of the core and prosthetic crown. An integral core of high density, low porosity alumina and a gold post are seated in a cavity in the implanted base and cemented thereto. A conventional gold crown is then fabricated and cemented onto the core. The implant functions successfully thereafter.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A dental, prosthetic, endosteal implant comprising:
a base comprised of a bio-compatible material, said base having first and second ends axially spaced along the longitudinal axis of said base and sidewalls which include serrations comprising alternating oblique and substantially planar surfaces, said substantially planar surfaces being substantially perpendicular to both the longitudinal axis of said base and the direction of the intended occlusal load and said oblique surfaces being disposed at an angle to the longitudinal axis of said base, the surface area of said planar surfaces nearest said second end being greater than the surface area of said planar surfaces nearest said first end, said first end being the outermost end upon implantation and said second end being the implanted end; and
a core extending from the first end of said base and configured to permit cooperative engagement with at least one prosthetic crown.

2. The implant of claim 1 wherein said bio-compatible material comprises alumina of high density.

3. The implant of claim 1 wherein said core and base comprise separate bodies which are joined together.

4. The implant of claim 1 wherein said serrations extend around the circumference of the base.

5. The implant of claim 1 wherein said base is substantially cylindrical.

6. The implant of claim 1 wherein said core is seated in a cavity in said base and attached thereto.

7. The implant to claim 5 wherein the longitudinal axes of said core and said base substantially coincide.

8. The implant of claim 1 wherein the depth of each of said serrations as defined by the lateral extent of each of said planar surfaces increases from said first end toward said second end.

9. The implant of claim 8 wherein the depth of said serrations increases at a uniform rate.

10. The implant of claim 1 wherein the depth of said serrations increases at a non-uniform rate.

11. The implant of claim 1 wherein said base is substantially rectangular in cross-section.

12. The implant of claim 1 wherein the depth of the serrations nearest said second end as defined by the lateral extent of each of said planar surfaces nearest said second end is at least about 50 percent greater than the depth of the serrations nearest said first end as defined by the lateral extent of each of said planar surfaces nearest said first end.

13. The implant of claim 12 wherein the depth of the serrations nearest said second end is at least about 100 percent greater than the depth of the serrations nearest said first end.

14. The implant of claim 2 wherein the density of said alumina exceeds about 93 percent.

15. The implant of claim 2 wherein said alumina is of high purity.

16. The implant of claim 1 wherein said base is tapered.

17. In a dental, prosthetic, endosteal implant comprising:
a base comprised of a bio-compatible material, said base having first and second ends axially spaced along the longitudinal axis of said base and side walls which include serrations comprising alternating oblique and substantially planar surfaces, said substantially planar surfaces being substantially perpendicular to both the longitudinal axis of said base and the direction of the intended occlusal load and said oblique surfaces being disposed at an angle to the longitudinal axis of said base, said first end being the outermost end upon implantation and said second end being the implanted end;
the improvement wherein the surface area of the planar surfaces nearest said second end is greater than the surface area of the planar surfaces nearest said first end.

18. The implant of claim 17 further including a core which extends from the first end of said base and is configured to permit cooperative engagement with at least one prosthetic crown.

19. The implant of claim 17 wherein the depth of each of said serrations as defined by the lateral extent of each of said planar surfaces increases from said first end toward said second end.

20. The implant of claim 19 wherein the depth of said serrations increases at a uniform rate.

21. The implant of claim 20 wherein the depth of said serrations as defined by the lateral extent of said planar surfaces increases at a non-uniform rate from said first end toward said second end.

22. The implant of claim 17 wherein the depth of the serrations nearest said second end as defined by the lateral extent of the planar surfaces nearest said second end is at least about 50 percent greater than the depth of the serrations nearest said first end as defined by the lateral extent of the planar surfaces nearest said first end.

23. The implant of claim 22 wherein the depth of the serrations nearest said second end is at least about 100 percent greater than the depth of the serrations nearest said first end.

24. A dental, prosthetic, endosteal implant comprising:
a base comprised of a bio-compatible material, said base having first and second ends axially spaced along the longitudinal axis of said base and side walls which include serrations comprising alternating oblique and substantially planar surfaces, said substantially planar surfaces being substantially perpendicular to both the longitudinal axis of said base and the direction of the intended occlusal load and said oblique surfaces being disposed at an angle to the longitudinal axis of said base, the surface area of said planar surfaces which, upon implantation, are adjacent to the aveolar crest being less than the surface area of said planar surfaces in the remaining portion of the base.

25. The implant of claim 24 wherein the depth of the serrations in the half of the base nearest to the first end as defined by the lateral extent of the planar surfaces in said half of the base nearest to the first end is less than the depth of the serrations in the half of the base nearest to the second end as defined by the lateral extent of the planar surfaces in said half of the base nearest to the second end.

26. The implant of claim 25 wherein the serrations in the half of the base nearest to the second end have substantially identical depths.

27. The implant of claim 24 wherein the depth of the serrations in the half of the base nearest to the second end as defined by the lateral extent of the planar surfaces in the half of the base nearest to the second end is at least about 50 percent greater than the depth of the serrations adjacent to the aveolar crest upon implantation as defined by the lateral extent of the planar surfaces adjacent to the aveolar crest upon implantation.

28. The implant of claim 27 wherein the depth of the serrations in the half of the base nearest to the second end is at least about 100 percent greater than the depth of the serrations in the half of the base nearest to the first end.

29. The implant of claim 24 wherein said bio-compatible material is alumina.

30. The implant of claim 24 further comprising a core extending from said first end and configured to permit cooperative engagement with at least one prosthetic crown.

31. The implant of claim 30 wherein the base and core comprise separate bodies which are joined together.

32. The implant of claim 24 wherein the minimum cross-sectional dimension of said base adjacent to the alveolar crest exceeds the minimum cross-sectional dimension of said base in the remaining portion of said base.

* * * * *